US012569354B2

(12) United States Patent
Rister et al.

(10) Patent No.: US 12,569,354 B2
(45) Date of Patent: Mar. 10, 2026

(54) ORTHOPEDIC BROACH

(71) Applicants:Smith & Nephew, Inc., Memphis, TN (US); Smith & Nephew Orthopaedics AG, Zug (CH); Smith & Nephew Asia Pacific PTE. Limited, Singapore (SG)

(72) Inventors: David W. Rister, Nesbit, MS (US); Mouhsin A. El-Chafei, Arlington, TN (US)

(73) Assignees: SMITH & NEPHEW, INC., Memphis, TN (US); SMITH & NEPHEW ORTHOPAEDICS AG, Zug (CN); SMITH & NEPHEW ASIA PACIFIC PTE. LIMITED, Singapore (SG)

( * ) Notice: Subject to any disclaimer, the term of this patent is extended or adjusted under 35 U.S.C. 154(b) by 0 days.

(21) Appl. No.: 18/787,077

(22) Filed: Jul. 29, 2024

(65) Prior Publication Data

US 2025/0041075 A1     Feb. 6, 2025

Related U.S. Application Data

(60) Provisional application No. 63/530,154, filed on Aug. 1, 2023.

(51) Int. Cl.
| | |
|---|---|
| *A61B 17/16* | (2006.01) |
| *A61B 17/72* | (2006.01) |
| *A61F 2/46* | (2006.01) |

(52) U.S. Cl.
CPC ........ *A61F 2/4603* (2013.01); *A61B 17/1668* (2013.01); *A61B 17/72* (2013.01)

(58) Field of Classification Search
CPC ................................................. A61B 17/1668
See application file for complete search history.

(56) References Cited

U.S. PATENT DOCUMENTS

| 5,665,091 A | 9/1997 | Noble et al. |
|---|---|---|
| 6,887,278 B2 | 5/2005 | Lewallen |

(Continued)

FOREIGN PATENT DOCUMENTS

| EP | 1216668 A2 | 6/2002 |
|---|---|---|
| EP | 1429691 B1 | 6/2008 |

(Continued)

OTHER PUBLICATIONS

Smith & Nephew, "Polarstem Cementless Stem System," 00766 V2 Mar. 15, 2015, 4 pages.

(Continued)

*Primary Examiner* — Nicholas W Woodall
(74) *Attorney, Agent, or Firm* — KDW Firm PLLC

(57) ABSTRACT

An improved orthopedic broach used to prepare an intramedullary canal of a patient's bone such as, for example, a patient's femur, to receive an orthopedic implant such as, for example, a hip stem implant. The broach has differential teeth or tooth patterns. In one preferred example, the broach includes three different types of teeth including diamond teeth, compaction teeth, and extraction teeth. The different teeth patterns being specifically arranged on the sides of the broach to optimize bone removal and bone compaction for a subsequently implanted hip stem implant. In addition, the different teeth patterns and locations enhancing rotational stability. As such, the broach is configured to compact bone in certain areas while removing bones in other areas, all while maintaining broach rotation.

23 Claims, 7 Drawing Sheets

(56)       References Cited

U.S. PATENT DOCUMENTS

| | | | |
|---|---|---|---|
| 6,974,482 | B2 | 12/2005 | Zhu |
| 7,060,102 | B2 | 6/2006 | Thompson |
| 7,175,668 | B2 | 2/2007 | Zweymuller |
| 7,214,246 | B2 | 5/2007 | Serbousek |
| 7,481,842 | B2 | 1/2009 | Noetzli |
| 7,494,509 | B1 | 2/2009 | Hershberger |
| 7,857,859 | B2 | 12/2010 | Willi |
| 8,252,062 | B2 | 8/2012 | Bandoh |
| 8,480,756 | B2 | 7/2013 | Frederick |
| 8,764,846 | B2 | 7/2014 | Grappiolo |
| 8,936,649 | B2 | 1/2015 | Huff |
| 9,192,477 | B2 | 11/2015 | Slater |
| 9,351,841 | B2 | 5/2016 | Meier |
| 9,358,115 | B2 | 6/2016 | Slater |
| 9,381,086 | B2 | 7/2016 | Ries |
| 9,750,850 | B2 | 9/2017 | Fonte |
| 10,405,984 | B2 | 9/2019 | McMinn |
| 10,426,623 | B2 | 10/2019 | Fridshtand |
| 10,842,915 | B2 | 11/2020 | Morrey |
| 11,259,932 | B2 | 3/2022 | Piecuch |
| 11,351,034 | B2 | 6/2022 | Satterthwaite |
| 2006/0184250 | A1 | 8/2006 | Bandoh |
| 2012/0265319 | A1 | 10/2012 | Prybyla |
| 2014/0081274 | A1* | 3/2014 | Huff ................... A61B 17/1659 |
| | | | 606/85 |
| 2014/0303742 | A1 | 10/2014 | Prybyla |
| 2014/0343685 | A1 | 11/2014 | Ranawat |
| 2016/0175109 | A1* | 6/2016 | Reu ........................... A61F 2/36 |
| | | | 606/85 |
| 2017/0086981 | A1 | 3/2017 | Bailey |
| 2019/0099191 | A1 | 4/2019 | Huff |
| 2021/0137688 | A1 | 5/2021 | Biggs |
| 2022/0117745 | A1 | 4/2022 | Roy |
| 2022/0249140 | A1 | 8/2022 | Favre |
| 2023/0157709 | A1* | 5/2023 | Gerges ............... A61B 17/1668 |
| | | | 606/80 |
| 2024/0081840 | A1* | 3/2024 | Endsley ............. A61B 17/1659 |

FOREIGN PATENT DOCUMENTS

| | | | |
|---|---|---|---|
| EP | 2708193 | A1 | 3/2014 |
| EP | 2386273 | B1 | 3/2016 |
| EP | 3295899 | B1 | 4/2019 |
| EP | 3244837 | B1 | 6/2019 |
| EP | 3714841 | B1 | 3/2022 |
| FR | 2961684 | A1 | 12/2011 |
| WO | 2023027952 | A | 3/2023 |

OTHER PUBLICATIONS

Smith & Nephew, "Anthology Primary Hip System," Innovative by design, 45860504 Jan. 7, 2007, 4 pages.

Smith & Nephew, "Polarstem Cementless and Cemented Stem System," Surgical Technique, 01217-en V5 Sep. 17, 2017, 32 pages.

Smith & Nephew, "Synergy Cementless Stem," Surgical Technique, 45610101 7138-0349 Nov. 4, 2004, 32 pages.

Smith & Nephew, "Anthology Primary Hip System," Surgical Technique, 71381440 REV0 Aug. 10, 2010, 28 pages.

Stryker, "Insignia Hip Stem," Data driven design aligned to your approach, Insign-PG-1_31966, 2021, 8 pages.

DePuy Synthes, "Actis Total Hip System," Surgical Technique, 160929-201130 EMEA, 2016, 20 pages.

Zimmer Biomet, "Avenir@ Femoral Hip System," 0725.1-GLBL-en-REV1016, 2016, 12 pages.

Smith & Nephew, "Polarstem Cementless and CementedStem System," Surgical Technique, 01217-en (1513) V4 Jan. 16, 2016, 32 pages.

Johanna Batz et al., "The influence of broach design on bone friction and osseodensification in total hip arthroplasty," Clinical Biomechanics 73 (2020), Dec. 2019, 234-240.

Andrew Jacobs, BS et al., "The effects of femoral stem misalignment and how next generation implant systems can help improve postperative outcomes," 2022, 15 pages.

International Search Report and Written Opinion for International Application No. PCT/US2022/040849, filed on Aug. 19, 2022, 9 pages.

European Patent Office, European Search Report, dated Dec. 16, 2024; 10 pages.

* cited by examiner

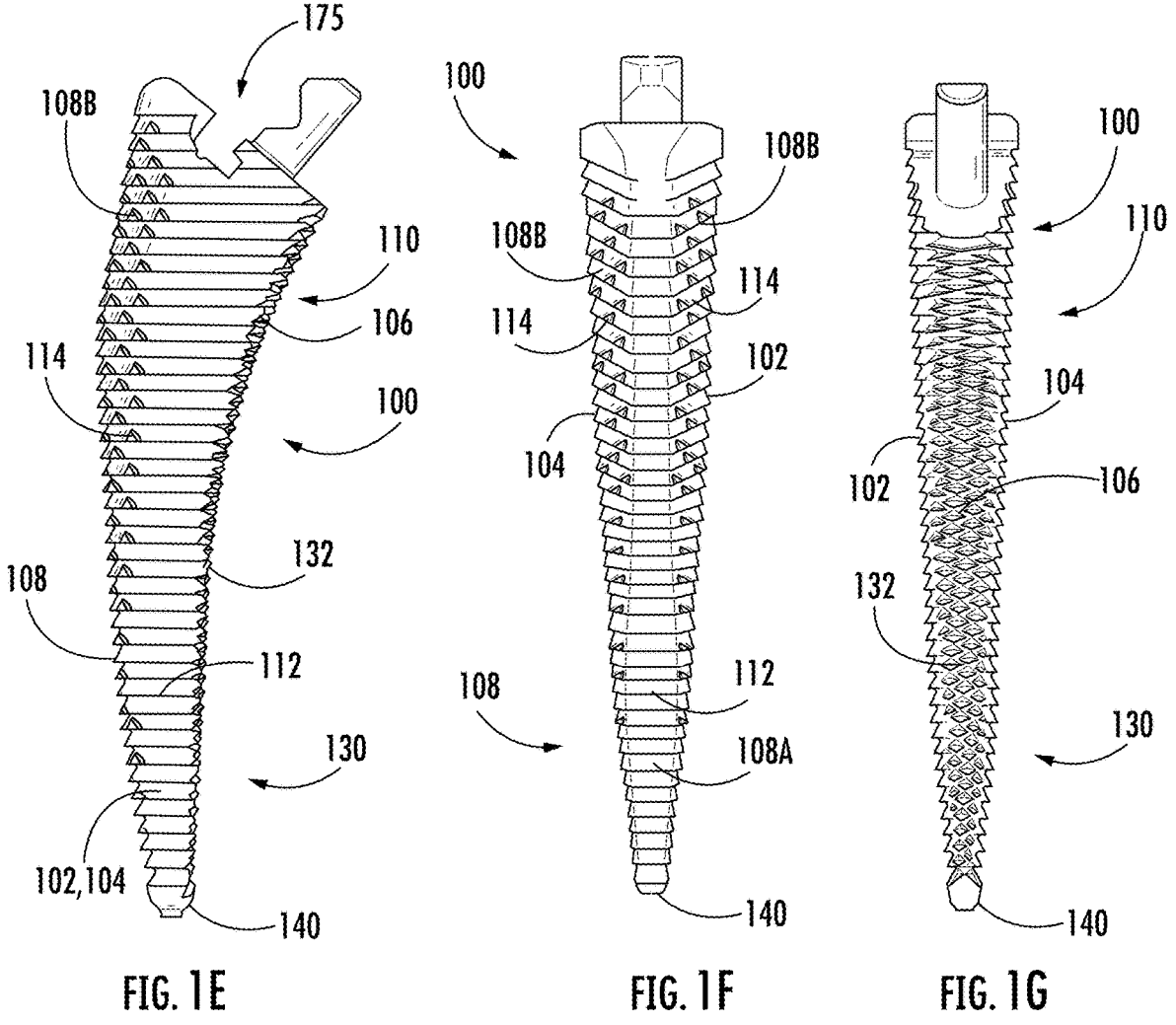
FIG. 1E                    FIG. 1F                    FIG. 1G

320

325

310

300

308

306

330

302

340

ORTHOPEDIC BROACH

CROSS-REFERENCE TO RELATED APPLICATIONS

This is a non-provisional of, and claims the benefit of the filing date of, U.S. provisional patent application No. 63/530,154, filed Aug. 1, 2023, entitled "Orthopedic Broach" the entirety of which application is incorporated by reference herein.

FIELD OF THE DISCLOSURE

The present disclosure relates generally to orthopedic devices and instruments, and more particularly to an orthopedic broach for preparing a patient's intramedullary canal to receive an implant such as, for example, a femoral hip stem implant.

BACKGROUND OF THE DISCLOSURE

Orthopedic implants are well known and commonplace in today's society. Orthopedic implants may be used, for example, to stabilize an injury, to support a bone fracture, to fuse a joint, and/or to correct a deformity. Orthopedic implants may be attached permanently or temporarily, and may be attached to the bone at various locations, including implanted within a canal or other cavity of the bone, implanted beneath soft tissue and attached to an exterior surface of the bone, or disposed externally and attached by fasteners such as screws, pins, and/or wires. Some orthopedic implants allow the position and/or orientation of two or more bone pieces, or two or more bones, to be adjusted relative to one another.

One type of orthopedic implant is a hip stem implant used to repair a hip joint. The hip joint is a frequent place for joint damage and/or injury. Hip stem implants can be implanted or otherwise associated with the bony anatomy for treating traumatic injuries, reconstructing joint function, or for other purposes. Hip stem implants may include an elongated insertion region (e.g., a stem), which can be at least partially inserted into an intramedullary canal of a patient's proximal femur.

In some instances, the success of the hip stem implant is dependent on how well the elongated insertion region or stem fits into the patient's bony anatomy (e.g., intramedullary canal of the patient's femur). For example, it is important that proximal portions of the elongated insertion region or stem of the hip stem implant fit tightly into the intramedullary canal (e.g., creating a press-fit between the proximal region of the implant and the inner surface of the intramedullary canal of the patient's femur), such that the stem loads proximal portions of the patient's femur, preventing bone loss through stress shielding and/or resorption (and potentially subsequent failure of the implant). It is also important that distal portions are properly positioned within the intramedullary canal; however, the fit should not be so tight as to prevent proximal loading.

A good fit between the hip stem implant and its associated bony anatomy may also help to prevent or lessen micromotion between the implant and the bone. Excessive micromotion may also lead to implant failure.

Moreover, when implanting a hip stem implant, proper preparation of the patient's intramedullary canal for receiving the hip stem implant is important. As a result, orthopedic instruments such as, for example, broaches, have been developed. A broach is used during, for example, hip arthroplasty surgeries. Surgeons use the broach to prepare an inner surface of a patient's intramedullary canal to receive the hip stem implant. The preparation of the intramedullary canal by the surgeon is designed to insure a proper fit between the patient's femur and the hip stem implant.

Implantation of hip stem implants require accurate preparation of the bone or intramedullary canal in order to guarantee good contact between the hip stem implant and the patient's bone. Generally speaking, reducing the gaps or spaces between the hip stem implant and the patient's bone (e.g., between the outer surface of the implant and the inner surface of the intramedullary canal), while ensuring adequate stem contact in key areas of the intramedullary canal in anterior/posterior and medial/lateral directions improves initial stability and long-term bone ingrowth/fixation.

The intramedullary canal of the patient's bone (e.g., femur) may be prepared for implantation of the hip stem implant by broaching and reaming a resected end of the proximal femur. The intramedullary canal of the patient's femur can be prepared using a broach to provide a seat for the hip stem implant. Generally speaking, a broach is a cutting tool, which may be moved or manipulated in an axial direction to create, enlarge, prepare, etc. the cavity or intramedullary canal of the patient's bone. A broach can be used to create a cavity with a noncircular cross-section. It is suitable for preparing a portion of the intramedullary cavity that receives the hip stem implant, in particular to ensure that the tapered shape of the hip stem implant, which can be a complicated irregular shape, is properly matched by the shape of the inner surface of the patient's intramedullary canal. As will be appreciated by one of ordinary skill in the art, with the head of the patient's femur removed, the broach can be inserted into the intramedullary canal of the femur. Cancellous bone, which is softer and somewhat spongy, surrounds the intramedullary canal. Surrounding the cancellous bone is cortical bone, which is stronger. The broach can be used to cut into the bone.

Improper bone cavity preparation can lead to loosening of the hip stem implant over time (e.g., proximally fixed hip stem implants may loosen over time if bony fixation with the implant occurs away from the intended fixation regions on the hip stem implant). To further complicate matters, recent developments in hip stem implants has resulted in hip stem implants that include coated and non-coated sections of the hip stem implant.

Thus, it would be beneficial to provide an improved orthopedic broach that better matches the shape and design of the subsequently implanted hip stem implant. In addition, there remains a need for an improved broach that avoids, or at least minimizes, distal fixation of proximally coated hip stem implants. The present invention satisfies these needs and provides other benefits and advantages in a novel and unobvious manner.

SUMMARY OF THE DISCLOSURE

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

In accordance with one or more features of the present disclosure, an improved orthopedic broach is disclosed. The orthopedic broach is arranged and configured to prepare an intramedullary canal of a patient's bone to receive an implant such as, for example, a hip stem implant. The broach is arranged and configured to avoid, or at least minimize, distal fixation of the hip stem implant within the patient's intramedullary canal. In addition, the broach is arranged and configured to optimize preparation of the intramedullary canal so that a desired press-fit is achieved between the proximal region of the hip stem implant and the inner surface of the patient's intramedullary canal.

In some examples, the broach includes a differential tooth patten. That is, the broach includes a plurality of distinct tooth patterns. In one example, the broach includes first, second, and third tooth patterns wherein each of the tooth patterns is different or unique from the other tooth patterns. Exemplary tooth patterns include diamond teeth, compaction teeth, extraction teeth, or any combination thereof, all of which are described in more detail below. The various tooth patterns are arranged and configured in specific locations on the broach to achieve a specific purpose. In some examples, the teeth are arranged and configured to optimize the remaining bone within the patient's intramedullary canal to facilitate improved engagement with the subsequently implanted hip stem implant. In a specific example, the teeth are arranged and configured to optimize and prepare the bone for optimal fixation of the implant. The broach can help improve engagement with respect to proximally formed porous coated surfaces and/or anterior and/or posterior grooves, which may be formed on the anterior and posterior sides of the proximal region of the hip stem implant.

For example, the broach may include a first tooth pattern on a medial side thereof, the first tooth pattern arranged and configured as cutting teeth optimized to remove bone. A specific example of cutting teeth are diamond teeth or pyramid shaped teeth (terms used interchangeably herein without the intent to limit or distinguish). Diamond teeth are provided in order to cut or remove the patient's bone to avoid, or at least minimize, distal fixation of the subsequently implanted hip stem implant. Diamond teeth are arranged and configured to penetrate into and remove any bone that they come into contact with. This can create an envelope to facilitate proper positioning of the distal region along a medial side of the broach, and consequently, the final implant. This can also avoid bony fixation of the distal region of the medial side of the subsequently implanted hip stem implant within the intramedullary canal. The overall desire is to produce an envelope that minimizes or avoids a press fit of the distal region of the medial side of the hip stem implant within the intramedullary canal. A further desire is to create a preferential press fit in the proximal portion of the hip stem implant in, for example, the region corresponding to the anterior and posterior grooves and/or the porous coated region formed on the hip stem implant. Diamond teeth facilitate improved contact between the diamond teeth and the patient's cancellous bone along the medial arc to prevent, or at least resist, rotational movement (e.g., providing diamond teeth on the medial side of the broach, increases rotational stability of the subsequently implanted hip stem implant by preventing, or at least minimizing, rotation of the subsequently implanted hip stem implant within the intramedullary canal of the patient's bone).

In addition, the anterior and posterior sides of the broach include a second tooth pattern. In addition, portions of the lateral side of the broach may also include the second tooth pattern. The second tooth pattern may be arranged as compaction teeth. Compaction teeth are shaped and optimized to compact, as opposed to cutting or removing, the patient's bone on the inner surface of the intramedullary canal. Compaction teeth are configured to leave larger particles of bone at the boney interface with greater penetration and densification of local boney tissue. In various examples, compaction teeth may extend horizontally (e.g., compaction teeth may extend perpendicularly relative to a longitudinal axis of the broach). Thus arranged, the broach is arranged and configured to form horizontal parallel ridges on the inner surface of the patient's intramedullary canal. The ridges may be angled relative to the anterior and posterior grooves, which may be formed on the anterior and posterior sides of the subsequently implanted hip stem implant.

In addition, the broach may include a third tooth pattern. The third tooth pattern may be arranged as extraction teeth. In some examples, portions of the lateral side of the broach may include extraction teeth. In some examples, the transitional or chamfer surfaces of the lateral side with the anterior and posterior sides may include extraction teeth (e.g., angled transitional or chamfer surfaces formed at the intersection of the lateral side with the anterior and posterior sides). In some examples, the proximal region of the broach may include extraction teeth formed on the anterolateral and posterolateral aspects or regions thereof (e.g., extraction teeth are formed on the lateral side along transitional or chamfer surfaces with the anterior and posterior sides of the broach). Extraction teeth are configured to remove boney residue. Extraction teeth may be configured to preferentially achieve a press fit away from the adjacent bone at the "corners" of the broach where anterior, posterior, and lateral bone of greater surface density. Extraction teeth can help achieve an optimized or preferential press fit in the corresponding region of the hip stem implant.

In some examples, the remaining portions of the lateral side of the broach include compaction teeth.

In various examples, the orthopedic broach may be provided as part of, or operatively associated with, a system or a kit along with a subsequently implanted hip stem implant such as, for example, a hip stem implant. Alternatively, the orthopedic broach may be separately provided.

The hip stem implant may include a proximal region, a distal region, an anterior side, a posterior side, a medial side, and a lateral side. In various examples, the proximal region includes a porous coated and/or roughened surface or region. Additionally, or alternatively, the proximal region may include a plurality of grooves formed on the anterior and posterior sides of the hip stem implant.

The broach is generally sized and shaped similarly to the hip stem implant. The broach includes a proximal region, a distal region, an anterior side, a posterior side, a medial side, and a lateral side. In one preferred example, the broach includes three different types of teeth including diamond teeth, compaction teeth, and extraction teeth.

An orthopedic broach is disclosed. The orthopedic broach being arranged and configured to prepare an intramedullary canal of a bone. The broach comprising a body with a proximal portion and a distal portion, an anterior side, a posterior side opposite the anterior side, a medial side, and a lateral side opposite the medial side, the medial and lateral sides extending between the anterior and posterior sides, the lateral side comprising an anterolateral surface at an intersection of the lateral side with the anterior side and a posterolateral surface at an intersection of the lateral side with the posterior side, wherein the medial side comprises a plurality of diamond teeth and the anterolateral and posterolateral surfaces comprises a plurality of extraction teeth having a different shape as compared to the plurality of diamond teeth.

In any preceding or subsequent example, the anterior and posterior sides include a plurality of compaction teeth having a different shape as compared to both the plurality of diamond teeth and the plurality of extraction teeth.

In any preceding or subsequent example, at least portions of the lateral side include a plurality of compaction teeth.

In any preceding or subsequent example, the plurality of extraction teeth extend a full length of the body along an anterolateral corner and a posterolateral corner of the body.

In any preceding or subsequent example, the anterolateral and posterolateral surfaces are defined by the proximal portion only.

In any preceding or subsequent example, the plurality of compaction teeth extend substantially a full-length of the lateral side from the proximal portion to the distal portion of the body.

In any preceding or subsequent example, each of the plurality of compaction teeth are configured as parallel ledges extending horizontally from the lateral side to the medial side of the anterior and posterior sides of the broach.

In any preceding or subsequent example, the plurality of compaction teeth extend substantially a full-length of the anterior and posterior sides from the proximal portion to the distal portion of the body.

In any preceding or subsequent example, each of the plurality of extraction teeth are configured as horizontal teeth including an angled cutting flute relief passing there-through.

In any preceding or subsequent example, each of the plurality of diamond teeth include a pointed or spiked tip.

In any preceding or subsequent example, the plurality of diamond teeth extend substantially a full-length of the medial side from a proximal end to a distal end of the body.

In any preceding or subsequent example, the body includes a connection mechanism arranged and configured to couple the broach to one of a handle and an orthopedic impactor.

In any preceding or subsequent example, the body include a distal tip devoid of any teeth.

In some examples, the orthopedic broach comprises a body comprising a plurality of diamond teeth on a medial side thereof, a plurality of compaction teeth on anterior and posterior sides thereof, a plurality of extraction teeth on anterolateral and posterolateral surfaces thereof, and a plurality of compaction teeth on at least a portion of the lateral side, each of the diamond teeth, the extraction teeth, and the compaction teeth having a different shape as compared to the other teeth.

Examples of the present disclosure provide numerous advantages. For example, by providing a broach including a differential tooth pattern, the broach is arranged and configured to optimize the remaining bone within the patient's intramedullary canal. This facilitates improved engagement with the subsequently implanted hip stem implant, in particular with respect to proximally formed porous coated surfaces and/or anterior and/or posterior grooves. For example, the broach is optimized to ensure creation of any envelope such as, for example, a three-hundred-and-sixty-degree envelope about the distal region to provide distal clearance to avoid distal fixation (e.g., the distal portion of the broach is configured to avoid a distal press-fit in favor of abutting contact (i.e., slight contact but not to the level of a press-fit). Meanwhile, the broach facilitates a press-fit along the proximal region of the implant (e.g., transition may occur below the porous region of the subsequently implanted hip stem implant).

In addition, the broach is arranged and configured to provide surgeons with improved rotational stability. For example, the positioning of the diamond teeth and the extraction teeth enable surgeons to assess rotational stability. That is, during broaching, the surgeon can rotate the inserted broach. When properly sized, the broach will provide rotational resistance thereby indicating that the broach is properly sized. This can also signal to the surgeon that the patient's intramedullary canal has been adequately prepared. As such, the surgeon is provided with increased confidence that the corresponding subsequently implanted hip stem implant is properly sized and seated within the prepared intramedullary canal. This preparation should result in increased confidence by the surgeon that proper sizing of the implant has been achieved and an assessment that the subsequently implanted hip stem implant will sit properly within the patient's intramedullary canal.

Further features and advantages of at least some of the examples of the present invention, as well as the structure and operation of various examples of the present invention, are described in detail below with reference to the accompanying drawings.

BRIEF DESCRIPTION OF THE DRAWINGS

By way of example, specific examples of the disclosed device will now be described, with reference to the accompanying drawings, in which:

FIGS. 1E-1G illustrate alternate views of the orthopedic broach, FIG. 1E illustrating the anterior and posterior view of the orthopedic view, FIG. 1F illustrating the lateral view of the orthopedic view, FIG. 1G illustrating the medial view of the orthopedic view.

Figure 1A:
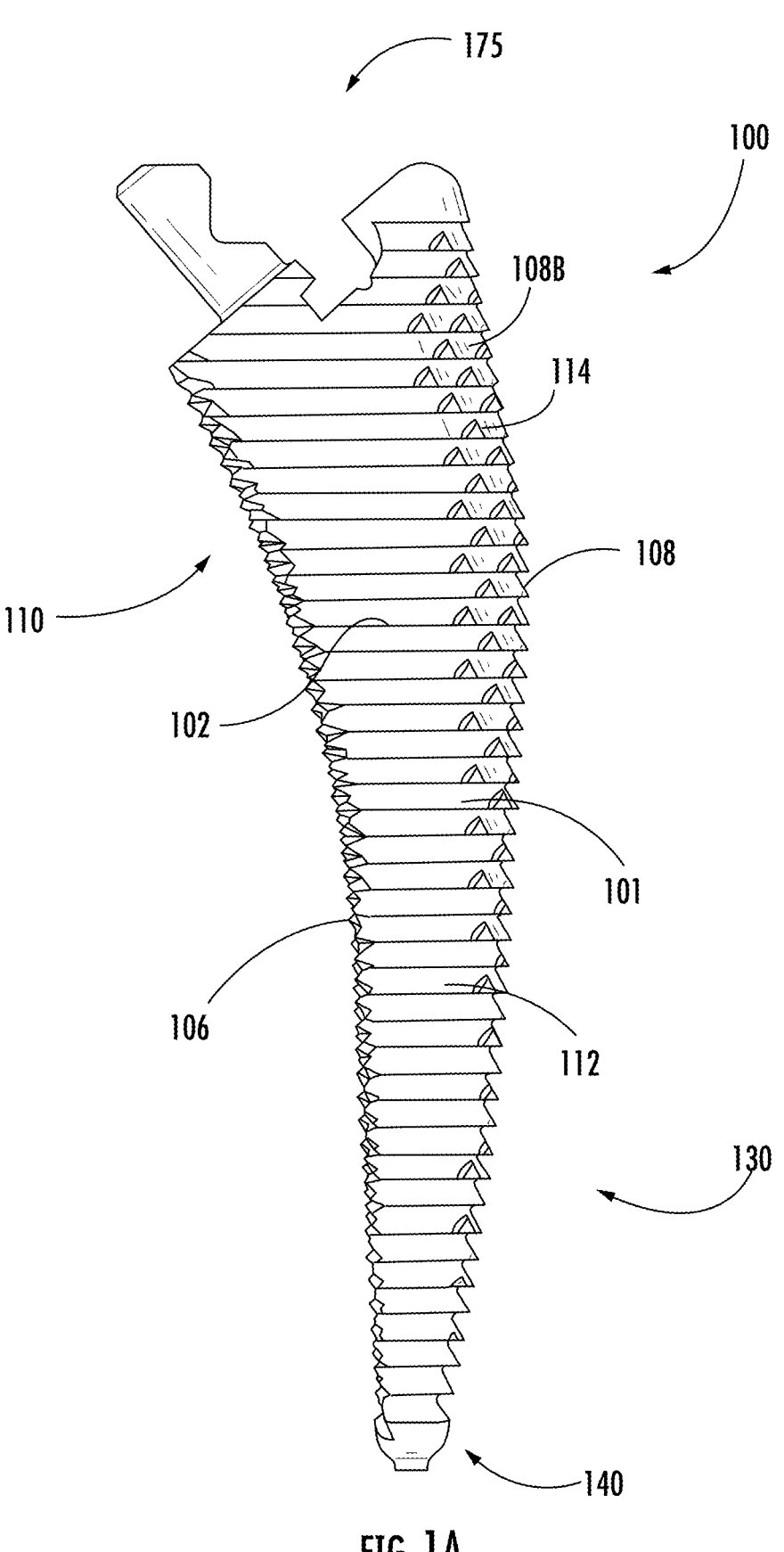
FIG. 1A is a side or anterior view of an example of an orthopedic broach that may be used in accordance with one or more features of the present disclosure, the anterior side including compaction teeth.

The drawings are not necessarily to scale. The drawings are merely representations, not intended to portray specific parameters of the disclosure. The drawings are intended to depict various examples of the disclosure, and therefore are not to be considered as limiting in scope. In the drawings, like numbering represents like elements.

DETAILED DESCRIPTION

Various features or the like of an orthopedic broach will now be described with reference to the accompanying drawings. It should be appreciated that the various features of the orthopedic broach may be used independently of, or in combination, with each other. The disclosed examples may take different forms and may selectively include one or more features, geometries, and/or dimensions described herein. As such, the broach should not be construed as being limited to the specific examples set forth herein. Rather, these examples are provided so that this disclosure will convey certain features, geometries, and/or dimensions to those skilled in the art.

The disclosed orthopedic broach is configured to optimize removal and/or preparation of the patient's bone to facilitate improved engagement with a subsequently implanted orthopedic implant such as, for example, a hip stem implant. The disclosed broach is arranged and configured to provide rotational stability. It can compact bone in certain areas while removing bone in other areas, all while maintaining rotational stability of the broach.

In some examples, the orthopedic broach includes a body having a differential tooth pattern. Different teeth patterns can be arranged and configured to prepare the patient's bone. For example, the broach includes first, second, and third different teeth patterns.

Figure 1B:
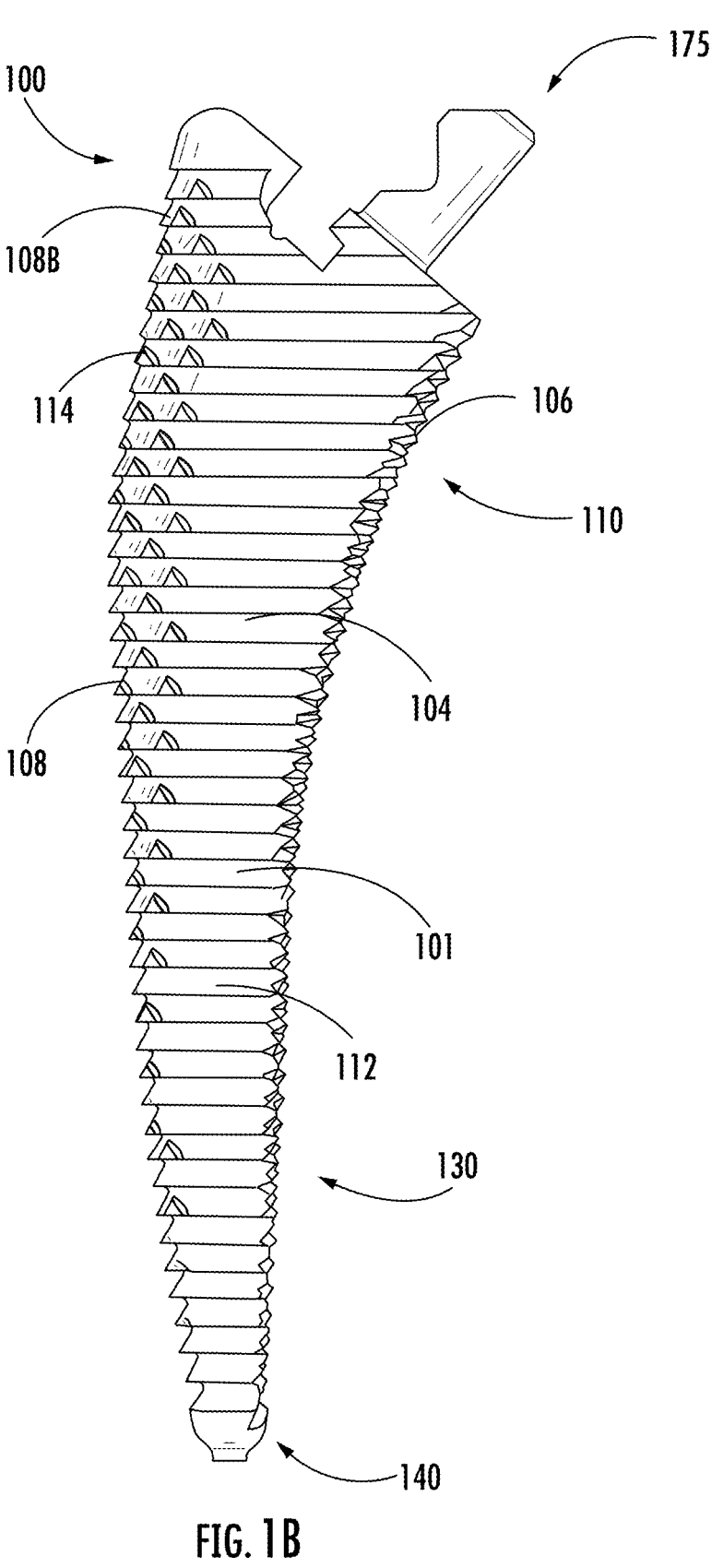
FIG. 1B is a side or posterior view of the orthopedic broach shown in FIG. 1A, the posterior side including compaction teeth.
Figure 1C:
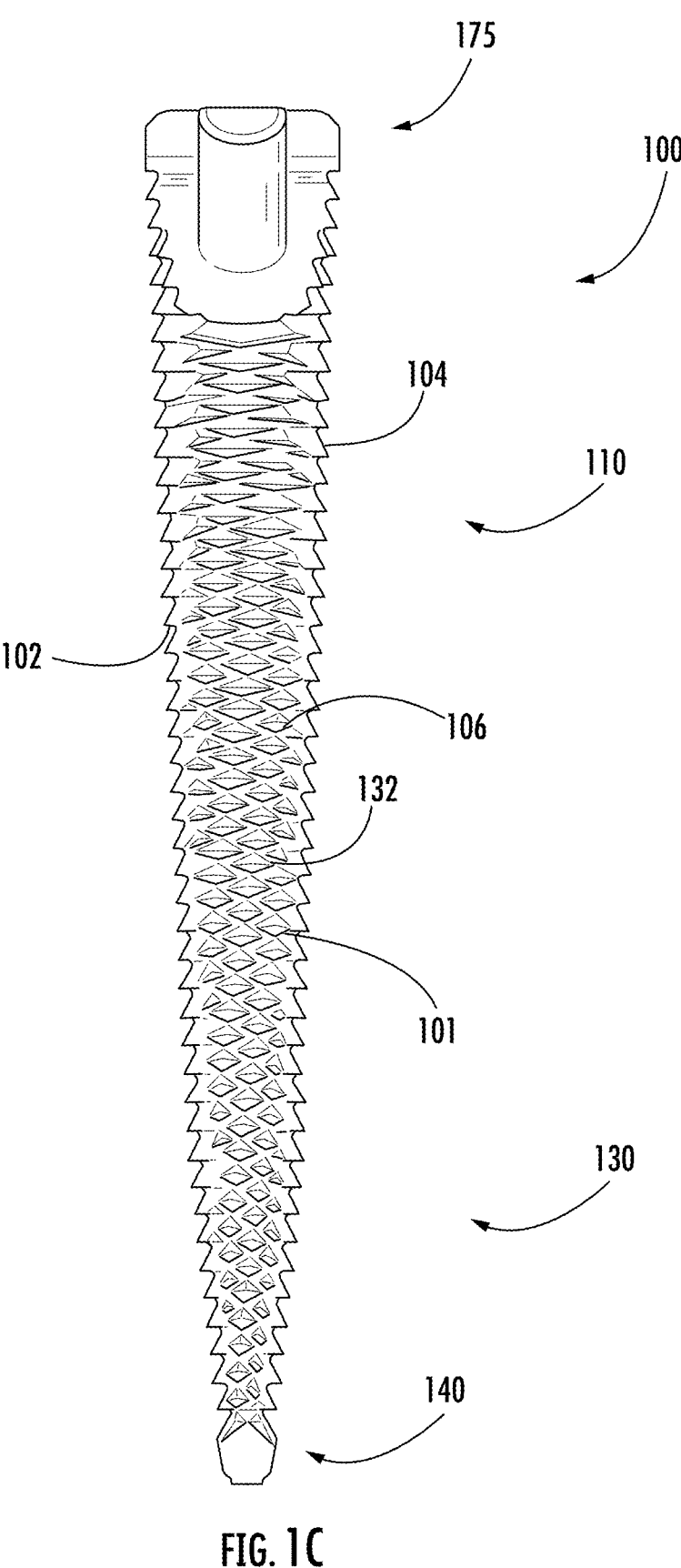
FIG. 1C is a side or medial view of the orthopedic broach shown in FIG. 1A, the medial side including diamond teeth.
Figure 1D:
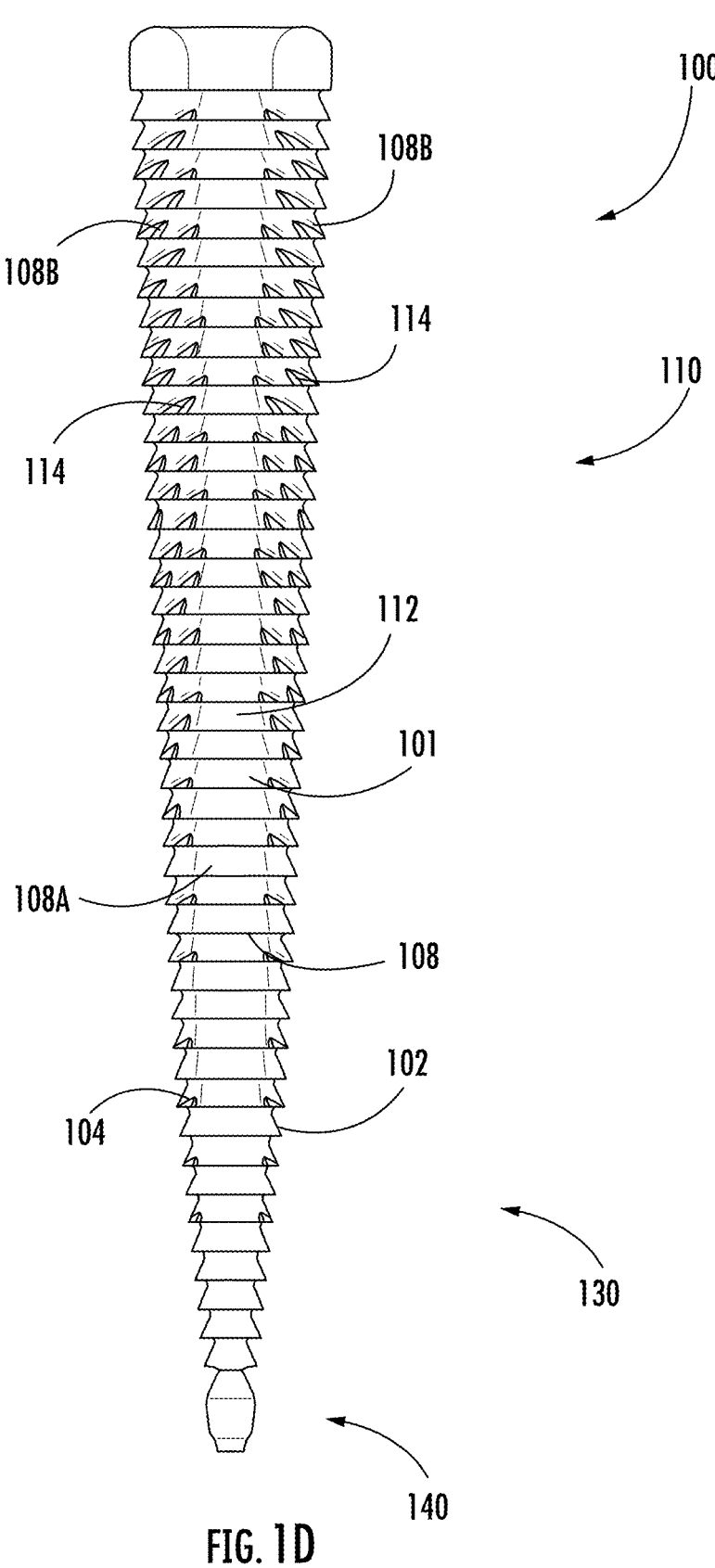
FIG. 1D is a side or lateral view of the orthopedic broach shown in FIG. 1A, the lateral side including compaction teeth and extraction teeth.
Figure 2A:
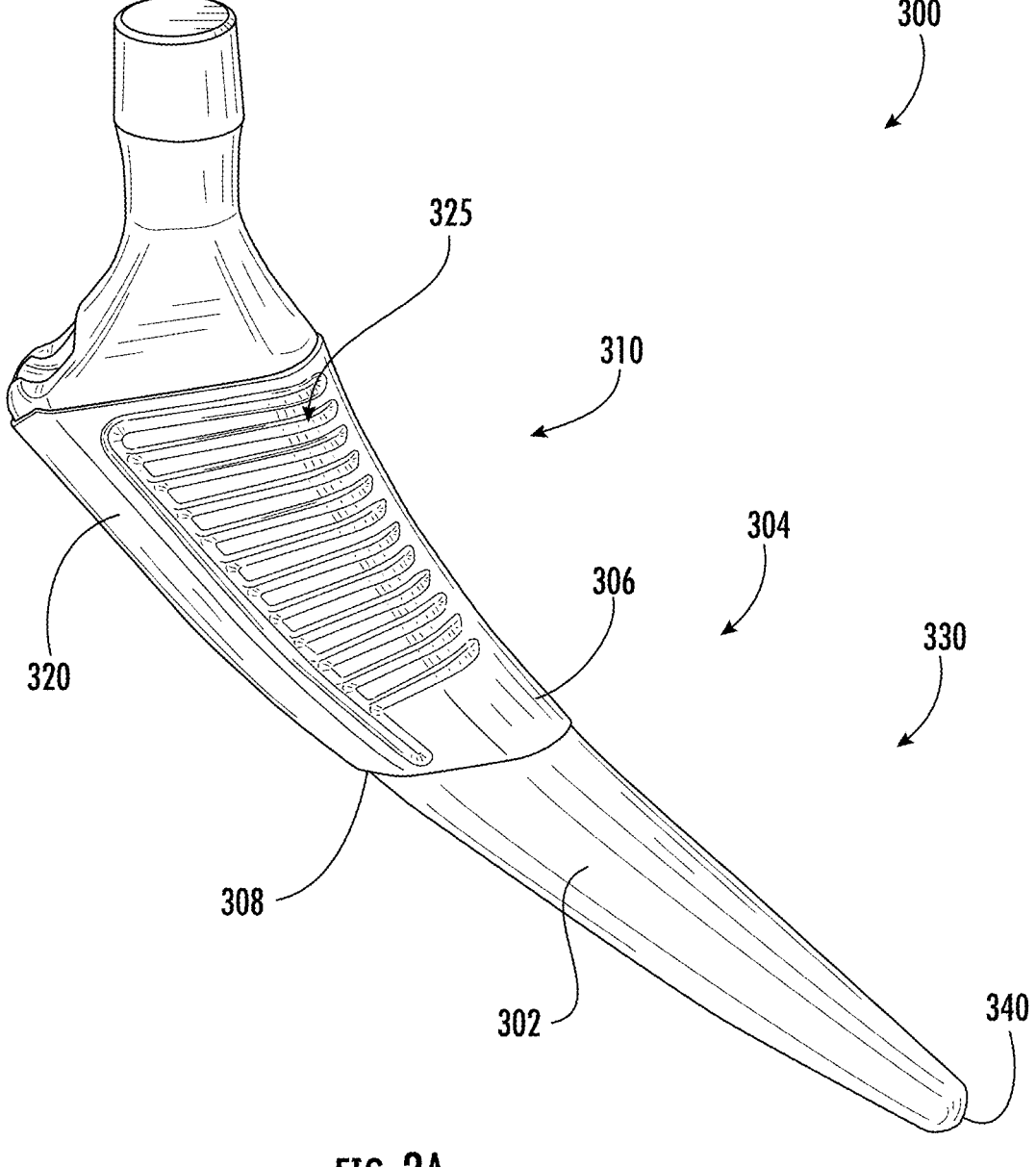
FIGS. 2A and 2B illustrate various views of an example of a hip stem implant that may be used with the orthopedic broach shown in FIGS. 1A-1G.
Figure 2B:
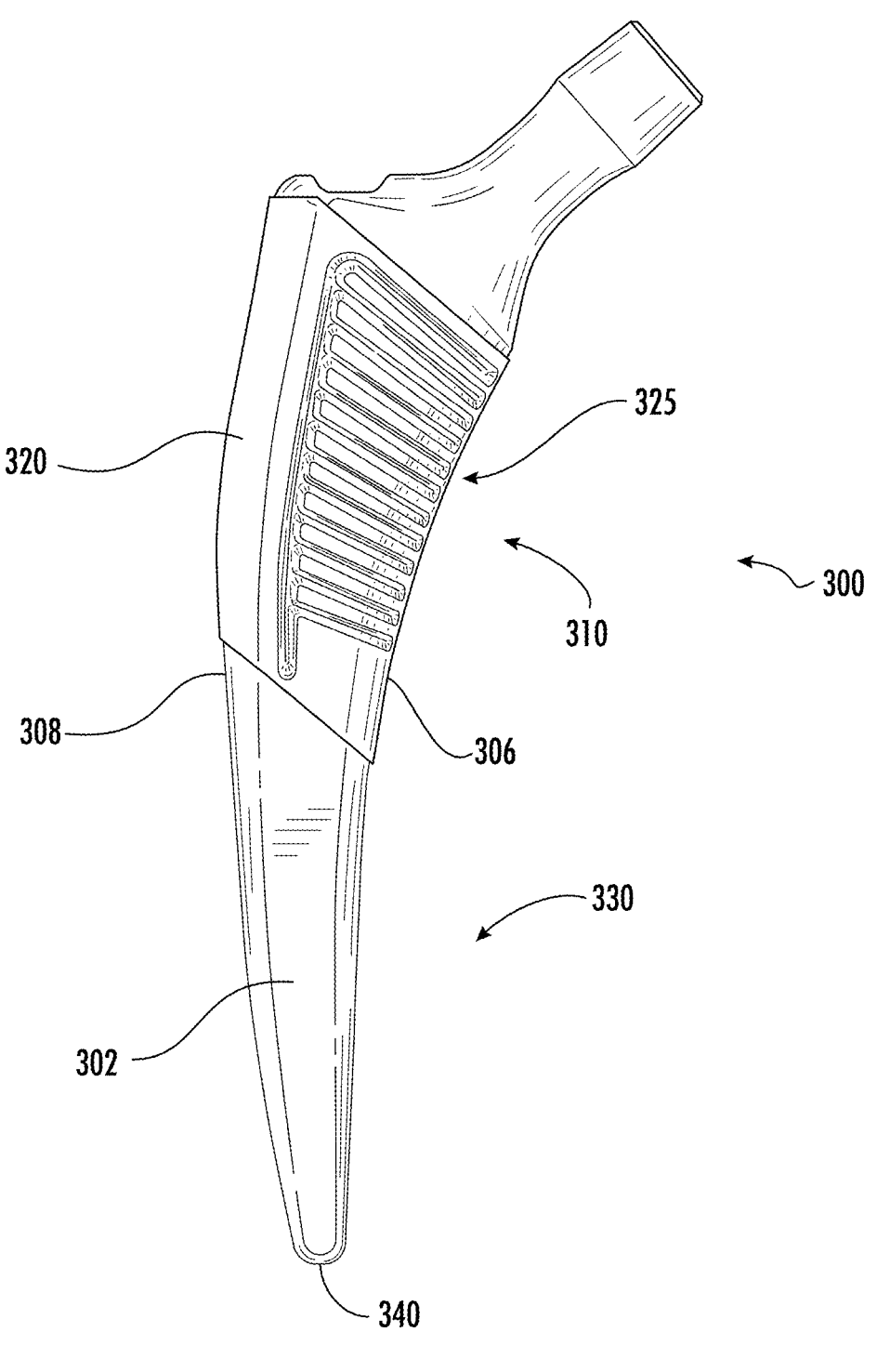

With reference to FIGS. 1A-1G, the broach 100 may be utilized to prepare an intramedullary canal of a patient's bone such as, for example, a patient's femur, to receive an orthopedic implant such as, for example, a hip stem implant. A non-limiting example of the disclosed broach is manufactured and sold under the name ACCUBROACH® from Smith & Nephew, Inc. A non-limiting example of a hip stem implant 300 is shown in FIGS. 2A and 2B. However, while the broach 100 of the present disclosure will be described in connection with this exemplary hip stem implant 300 (described in more detail in U.S. patent application Ser. No. 18/685,093, which is incorporated herein by reference, and which is manufactured and sold by Smith & Nephew, Inc. under the name CATALYSTEM® Primary Hip System), the broach 100 of the present disclosure is not so limited and may be used with any suitable implant now known or hereafter developed. As such, the broach should not be limited for use with any particular type or configuration of implant unless explicitly claimed.

In a specific example, the broach 100 may include three different types of teeth including diamond teeth 132, compaction teeth 112, and extraction teeth 114. In a preferred example, the broach 100 includes diamond teeth 132 formed on a medial surface or side 106 of the broach 100 to sequentially remove bone (terms surface and side used interchangeably herein without the intent to limit or distinguish). The broach 100 includes extraction teeth 114 along the anterolateral and posterolateral surfaces, aspects or regions 108B thereof (terms used interchangeably herein without the intent to limit or distinguish). The positioning of the diamond teeth 132 along the medial side 106 of the broach 100 and the extraction teeth 114 along the anterolateral and posterolateral regions 108B of the broach 100 enable surgeons to assess rotational stability of the broach 100 within the patient's intramedullary canal and/or provides surgeons with improved feedback/assessment of the final implant fitting and/or sizing.

With reference to FIGS. 2A and 2B, and as described in U.S. patent application Ser. No. 18/685,093, the subsequently implanted hip stem implant 300 may include a proximal region 310 and a distal region 330. The hip stem implant 300 also includes an anterior side 302, a posterior side 304, a medial side 306, and a lateral side 308. In various examples, the proximal region 310 includes, and is defined by, a porous coated and/or roughened surface or region 320 (terms used interchangeably herein without the intent to limit or distinguish). It is also possible for the anterior and posterior sides 302, 304 to include grooves 325 formed therein. Grooves 325 have been shown to facilitate improved engagement with the remaining patient's bone following the broaching process. The grooves 325 may be angled (e.g., angled downwards) along the anterior and posterior sides 302, 304 of the hip stem implant 300 from the lateral side 308 toward the medial side 306. In some examples, the grooves 325 may extend to, and along, at least a portion of the medial side 306 of the hip stem implant 300.

The disclosed broach 100 includes a body 101 having a proximal region 110 and a distal region 130. The body 101 includes an anterior side 102, a posterior side 104, a medial side 106, and a lateral side 108, wherein the anterior and posterior sides 102, 104 extend between the medial and lateral sides 106, 108. The body 101 includes an outer surface having a size and shape substantially similar to the hip stem implant for which it is designed to prepare the bone cavity to receive.

The broach 100 includes differential teeth or tooth patterns. In one preferred example, the broach 100 includes a plurality of different types of teeth such as, for example, three different types of teeth including diamond teeth 132, compaction teeth 112, and extraction teeth 114.

Diamond teeth 132 are arranged and configured to cut and remove bone. They are optimized to cut and remove bone while providing localized compaction greater than extraction teeth 114 and less than compaction teeth 112. Diamond teeth 132 may be characterized as having a pointed or spiked tip. For example, diamond teeth 132 may include a trough and a protrusion with an end in the form of a tip. Each tip may be abutted by a plurality of surfaces that protrude from surrounding troughs. With diamond teeth 132, each of these side surfaces converge at a point in the form of a sharp tip. Diamond teeth 132 are arranged and configured to promote cutting of bone.

Extraction teeth 114 may be characterized as having ridges, where the ridges have a sharp edge. The shape of the extraction teeth 114 provides a chip breaking function that improves bone removal to create a surface in the bone that mimics the shape of the hip implant to be placed after use of the broach. Chip breaking functionality allows for debris generated during the broaching process to escape the broach—bone interface. This prevents build-up of debris between the teeth and subsequent pressing of the debris into the intermedullary wall (compaction). Chip breaking functionality allows improved bone removal to create a surface in the bone that mimics the shape of the hip implant to be placed after use of the broach. Extraction teeth 114 may be configured as horizontal teeth with an angled "cutting flute" relief passing through for effective removal of boney residue intended to preferentially achieve press fit away from the adjacent bone at, for example, the "corners" of the broach where anterior, posterior, and lateral bone of greater surface density to achieve an optimized or preferential press fit in the corresponding region of the hip stem implant. For example, extraction teeth 114 may include repeating troughs and protrusions with ends in the form of ridges, where the ridges may have a sharp edge or a blunt edge extending along a length. Each ridge may be abutted by a plurality of surfaces that protrude from troughs of the teeth.

Compaction teeth 112 may be characterized as having flat ends or surfaces, and may be characterized as ridges, ledges, or steps. Compaction teeth 112 include, or form, parallel ridges, ledges or steps (terms used interchangeably herein without the intent to limit or distinguish). Compaction teeth 112 are optimized to improve bone compaction while minimizing raking of the bone. Compaction teeth 112 do not include a pressure relief mechanism (unlike extraction teeth/chip breakers). This arrangement means that bony debris is pressed into the intermedullary wall of the patient's bone as it builds up during the broaching process. The generally tapered geometry of the body of the broach and backside angle of the teeth minimize removal of debris during broach removal. For example, compaction teeth 112 may include a pattern of repeating troughs and protrusions with ends in the form of flat ridges. The flat ridges may have a length that extends in an unbroken fashion across a width of a surface region that includes the compaction teeth. Contrary to extraction teeth 114, compaction teeth 112 do not include a chip breaking function. Compaction teeth 112 operate to reduce the tendency to extract bone and improve bone compaction for greater stability.

As shown, the body 101 includes a connection mechanism 175 arranged and configured to enable the broach 100 to be coupled to a handle, an orthopedic impactor, etc. In some examples, the connection mechanism 175 may be provided in the form of a post. Alternatively, the connection mechanism 175 may be provided in the form of a cavity, a pocket, etc. Alternatively, any suitable connection mechanism now known or hereafter developed may be used.

The distal region 130 may terminate in a distal tip 140. The distal tip 140 may be devoid of any teeth. This shape can minimize perforation of the patient's cortices by the distal tip 140 during broaching.

Each of the diamond teeth 132, compaction teeth 122, and extraction teeth 114 are specifically arranged and configured, depending on their location, to optimize improved engagement of the prepared bone with a hip stem implant. In the specific examples shown, the broach 100 includes diamond teeth 132 on the medial side 106 thereof. In the specific examples shown, the broach 100 includes extraction teeth 114 along the posterior and anterior transitional or chamfer regions or surfaces 108B with the lateral side 108 (e.g., extraction teeth 114 are positioned on the angled transitional or chamfer surfaces 108B formed at the intersection of the lateral side 108 with the anterior and posterior sides 102, 104). Thus arranged, the broach 100 is optimized to ensure distal clearance (e.g., optimized to create an envelope (e.g., a 360-degree envelope)) to avoid distal fixation. This can facilitate a press-fit along the proximal region of the implant.

In addition, and/or alternatively, the broach 100 is arranged and configured to ensure rotational stability of the broach 100 within the intramedullary canal of the patient's bone during use. The positioning of the diamond teeth 132 and the extraction teeth 114 enable surgeons to determine rotational stability. That is, during broaching, the surgeon can rotate the inserted broach 100. When properly sized, the broach 100 provides rotational resistance thereby indicating that the broach 100 is properly sized and the patient's intramedullary canal has been adequately prepared. As such, the surgeon is provided with an assessment that the subsequently implanted hip stem implant will sit properly within the patient's intramedullary canal.

It has been found that the specific combination of the tooth patterns described herein provides a particularly reliable, confident, and stable implantation. The specific broach shown and described includes a combination of the three types of teeth described, positioned along various and specific portions of the broach body. Although it is possible for changes of these locations and tooth patterns to be made, a specific embodiment of the broach will now be described. As shown by FIGS. 1C and 1G, the medial side 106 of the broach 100 includes diamond teeth 132 having a first tooth pattern. As best illustrated in FIGS. 1A, 1B, and 1E, the anterior and posterior sides 102, 104 include compaction teeth 112 having a second tooth pattern. FIGS. 1D and 1F show that the lateral side 108 includes regions 108A having compaction teeth 112 and regions 108B having extraction teeth 114 having a third tooth pattern. Extraction teeth 114 having the third tooth pattern are positioned on or adjacent to the corners, edges, or intersection between the anterior and posterior sides 102, 104 and the lateral sides 108 (e.g., transitional or chamfer surfaces or regions 108B between the anterior and posterior sides 102, 104 and the lateral side 108). In some examples, the proximal region 110 may include extraction teeth 114 formed on the anterolateral and posterolateral regions 108B thereof. Thus arranged, the lateral side 108 of the broach 100 includes compaction teeth 112 and extraction teeth 114 in, at least, the proximal region 110 thereof.

FIGS. 1C and 1G illustrate that the medial side 106 of the broach 100 includes diamond teeth 132 with a first tooth pattern that differs from the second and third tooth patterns. In preferred examples, the diamond teeth 132 may extend a full length, or substantially full-length, of the medial side 106 from the proximal end to the distal end of the broach 100.

The diamond teeth 132 formed on the medial side 106 of the broach 100 optimize the broach 100 to facilitate removal of any bone portions protruding on the inner surface of the intramedullary canal of the patient's bone during insertion of the broach 100 therein. Diamond teeth 132 have been found to perform better in rasping (for clearance) and gripping into bone when the broach 100 has been fully seated within the canal of the patient's bone, thereby providing rotational stability. In addition, by providing diamond teeth 132 on the medial side 106 of the broach 100, increased rotational stability is provided to prevent, or at least assist in preventing, rotation of the subsequently implanted hip stem implant 300 within the intramedullary canal of the patient's bone. Moreover, diamond teeth 132 may provide a lower coefficient of friction with the patient's bone, which provides an advantage for the portion of the broach intended to penetrate into the patient's tissue.

As previously mentioned, the broach 100 is arranged and configured to produce a three-hundred and sixty-degree envelope that minimizes or avoids a press fit of the distal region 330 of the hip stem implant 300 within the intramedullary canal. The disclosed broach 100 is configured to avoid a distal press-fit in favor of abutting contact, which does not rise to the level of a press-fit, to create a preferential press fit in the proximal region 310 of the hip stem implant 300. For example, the disclosed broach 100 is configured to create a preferential press fit in the porous coated region 320. In addition, or alternatively, the disclosed broach 100 is configured to create a preferential press fit in the region containing the anterior and posterior grooves 325. In one example, the geometry of the distal region 130 of the broach 100 may be sized and configured to be larger than the distal region 330 of the hip stem implant 300 to create the envelope or clearance. The distal region 130 of the broach 100 may be configured to remove bone leaving the envelope or a contact condition between the distal region 330 of the hip stem implant 300 that extends from the distal tip 340 of the hip stem implant 300 up to the termination of the porous coating region 320 formed on the proximal region 310 of the hip stem implant 300. This transition is intended to avoid any kind of press fit condition with the distal region 330 of the hip stem implant 300 by providing a distal clearance between the inner surface of the patient's intramedullary canal and the distal region 330 of the hip stem implant 300 (e.g., loosely fitted distal region). In turn, this helps achieve and/or promote a proximal press fit hip stem implant 300. As a result, excessive fit in long term on-growth, which may result in distal thigh pain or loosening of the distal stem due to proximal stem stress shielding, can be avoided. Also, extending the diamond teeth 132 on the distal region 130 of the broach 100 allows for cortical bone removal at the mid-body of the hip stem implant, proximal to the isthmus and distal to the lesser trochanter.

With reference to FIGS. 1A, 1B, and 1E, the compaction teeth 112 may extend a full length, or substantially full-length, of the anterior and posterior sides 102, 104 from the proximal end to the distal end of the broach 100. The compaction teeth 112 are configured to compact the bone on the inner surface of the intramedullary canal as opposed to cutting into it or removing it. The greater number and size of boney residue particles from the compaction teeth 112 provide greater degree of broaching residue such that, for example, the angled geometry of the anterior and posterior grooves 325 formed on the hip stem implant 300 create a generally positive rake angle. This can more effectively "peel" residue into the anterior and posterior grooves 325. This process is intended to provide the opportunity for osseoinduction into the anterior and posterior grooves 325 to provide long term implant stability. Greater densification depth from the compaction teeth 112 is also intended to provide a firmer boney interface for initial femoral stem press-fit fixation.

As shown in FIGS. 1A, 1B, and 1E, compaction teeth 112 may extend horizontally across the anterior and posterior sides 102, 104 of the broach 100. Compaction teeth 112 may extend horizontally across the anterior and posterior sides 102, 104 between the medial and lateral sides 106, 108 including the anterolateral and posterolateral regions 108B. Compaction teeth 112 are configured to enable bone preservation and stability. During insertion of the broach 100 into the patient's intramedullary canal, the compaction teeth 112 push or compact the patient's bone. This creates an improved envelope for subsequent implantation of the hip stem implant.

During insertion of the broach 100, the compaction teeth 112 leave a pocket in the patient's bone arranged and configured to interact with, for example, the porous coated region 320 and/or the anterior and/or posterior grooves 325 formed on the hip stem implant 300. Compaction teeth 112 compact and move the contacted bone, while also leaving some cancellous bone to engage, for example, the porous coated region 320 and/or the anterior and posterior grooves 325 of the implant 300.

As shown, compaction teeth 112 may form horizontally extending, parallel ridges in the patient's bone (e.g., the anterior and posterior tooth pattern may be generally perpendicularly arranged relative to a longitudinal axis of the subsequently implanted hip stem implant 300), which may be angled relative to the anterior and posterior grooves 325 formed on the subsequently implanted hip stem implant 300. Perpendicularly arranged compaction teeth 112 compact and/or densify the cancellous bone, leaving a slight stair-step pattern. The corresponding opposing anterior and posterior sides 302, 304 of the implant 300 may include grooves 325 that are angled with respect to the arrangement of the perpendicularly arranged compaction teeth 112 on the broach 100, thereby producing a cross-hatching pattern. The compaction teeth 112 push the patient's bone on the anterior and posterior sides of the patient's intramedullary canal, which, during implantation of the hip stem implant 300, rakes the patient's bone creating an improved envelope for receiving the stem of the hip stem implant 300 while leaving pockets for the grooves 325 formed on the hip stem implant 300 to fill with bone-in-growth (e.g., ridges are left in the patient's bone that can be scrapped by the grooves 325 formed on the hip stem implant 300 eliminating, or at least minimizing, any gap that bone needs to bridge).

Post broaching with the hip stem implant 300 positioned within the intramedullary canal of the patient's bone, the compaction teeth 112 formed on the anterior and posterior sides 102, 104 of the broach 100 are configured to form a cross-hatching with the grooves 325 formed on the anterior and posterior sides 302, 304 of the hip stem implant 300. During implantation, the hip stem implant 300 scrapes or rakes the peaks of the stair-step cavity (e.g., parallel ridges) left behind from the broaching process into the recess of the grooves 325 formed on the anterior and posterior sides 302, 304 of the hip stem implant 300. This can provide accelerated bony in-growth and increased resistance to subsidence and rotational micromotion.

The parallel ridges formed on the patient's intramedullary cavity by the broaching process can be subsequently raked during implantation of the hip stem implant 300. Providing a broach with teeth shaped as described has been found to minimize any gaps that may remain between the raked bone and the anterior and posterior grooves 325 in the hip stem implant 300 thereby facilitating improved long-term stability.

Providing compaction teeth 112 on the anterior and posterior sides 102, 104 of the broach 100, the inner bony surface of the patient's intramedullary canal is compacted to interact more fully and precisely with the final implant. The interface between the implant 300 and the patient's bone (cortical/cancellous) is addressed. The result is to compact and densify the bony apposition to the porous coated region 320 formed on the implant 300, while clearing the diaphysis of the intramedullary canal of the patient's bone to contact/support the distal region 330 of the hip stem implant 300 without a press fit. This allows, a differential press fit to the proximal in-growth surface on the hip stem implant 300. This avoids a distal "pedastool" or press fit which may lead to long term stress shielding of the proximal femur and implant loosening.

As shown by FIGS. 1D and 1F, the lateral side 108 of the of the broach 100 may include regions 108A having compaction teeth 112. Thus, the lateral side 108 includes regions 108A having compaction teeth 112 similar to the anterior and posterior sides 102, 104. The lateral side 108 of the broach 100 may also include regions 108B that include extraction teeth 114 having a third tooth pattern. As illustrated, the lateral side 108 may include chamfer or transitional surfaces or regions 108B between the lateral side 108 and the anterior and posterior sides 102, 104. In some examples, these chamfer or transitional surfaces or regions 108B are positioned along, extend from, the proximal region 110 of the broach 100. As illustrated, the chamfer or transitional surfaces or regions 108B between the lateral side 108 and the anterior and posterior sides 102, 104 define regions 108B including extraction teeth 114 having the third tooth pattern. Along at least the proximal region 110 of the broach 100, the lateral side 108 includes regions 108B (e.g., chamfered or transitional surfaces) that include extraction teeth 114 positioned along the corners, edges, or intersection between the anterior and posterior sides 102, 104 and the lateral side 108. More specifically, the lateral side 108 includes extraction teeth 114 formed on the anterolateral and posterolateral aspects thereof. Location of the extraction teeth 114 is arranged and configured to correspond to the proximal press-fit section of the same-sized femoral stem in the antero- and postero-lateral aspects or regions.

In this example, the extraction teeth 114 are arranged and configured as corner teeth. They function to cut, extract, and/or remove the patient's bone that contact the extraction teeth 114 during broaching. As such, the extraction teeth 114 may be referred to as chip-breakers, which are arranged and configured to cut into the patient's bone (e.g., optimized to remove cancellous bone). The extraction teeth 114 can provide the anterolateral and posterolateral aspects of the proximal region of the broach 100 with interrupted cuts to form a press fit in the corresponding proximal, anterolateral and posterolateral region where the implant will be seated. This can also reduce densification of the bone. The interrupted cuts facilitate a path for bone extrusion during broaching and a more aggressive pattern that allows relief of proximal cortical bone in the patient's femur. Extraction teeth 114 may be configured to provide an annular grind, while incorporating a relief to allow material to flow out during the broaching process.

Extraction teeth 114 extract the patient's bone on the lateral side of the intramedullary canal of the patient's bone. Extraction teeth 114 remove any bone on the lateral side of the intramedullary canal on the patient's bone with minimal compaction to promote clearance (e.g., prevent lateralization, which may cause the broach to be inserted crooked (e.g., at an angle)). Extraction teeth 114 facilitate clearance during implantation of the hip stem implant 300 by preventing, or at least minimizing, lateralization. Extraction teeth 114 assist in clearing bone in the anterolateral and posterolateral areas of the intramedullary canal of the patient's bone. Thus arranged, soft tissue may be spared.

As best illustrated in FIGS. 1E and 1F, the compaction teeth 112 on the lateral side 108 may extend a full length, or substantially full-length, of the lateral side 108 from the proximal end to the distal end of the broach 100. The extraction teeth 114 may extend from the proximal end towards the distal end. The extraction teeth 114 may extend a full length, or substantially full-length, from the proximal end to the distal end of the lateral side 108. Extraction teeth 114 may be placed on the corners between the anterior side 102 and the lateral side 108 (e.g., anterolateral corner) and between the posterior side 104 and the lateral side 108 (e.g., posterolateral corner) for the entire length of the broach 100. Alternatively, the extraction teeth 114 may extend from 25 percent to 75 percent or more of the length of the lateral side 108. In some specific examples, the extraction teeth 114 extend from 50 percent to 75 percent of the length of the lateral side 108. In a further specific example, the extraction teeth 114 extend approximately 65 to 70 percent of the length of the lateral side 108. In addition, and/or alternatively, in some examples, each of the chamfer surfaces or regions 108B containing the extraction teeth 114 may extend from 10 to 40 percent of the width of the lateral side 108 at the proximal end. In some examples, each of the chamfer surfaces or regions 108B containing the extraction teeth 114 may extend from 20 to 35 percent of the width of the lateral side 108 at the proximal end. In a further specific example, the extraction teeth 114 extend approximately 30 to 35 percent of the width of the lateral side 108 at the proximal end. In a further specific example, the extraction teeth 114 cover approximately 33 percent of the lateral side 108.

The broach may be manufactured from any suitable material now known or hereafter developed. For example, the broach may be manufactured entirely from stainless steel. Alternatively, other metals may be used. Additionally, in some examples, the broach may be made from a hard plastic, such as PEEK.

The broach may be formed using any desired or appropriate methodologies or technologies now known or hereafter developed. For example, the broach may be manufactured using any now known or hereafter developed additive manufacturing technique. By way of some, non-limiting known techniques, the broach could be manufactured from selective laser sintering (SLS), direct metal laser sintering (DMLS), electron beam melting (EBM), selective laser melting (SLM), three-dimensional printing, or the like. For example, the broach may be formed as a monolithic or integral component. In other examples, an additive manufacturing technique such as, for example, electron beam melting methods or methods that use lasers to subtract or remove select portions of material from an initially solid material may be used. In other examples, portions or all, of the broach can be formed using casting or other technologies or methods.

While the present disclosure refers to certain examples, numerous modifications, alterations, and changes to the described examples are possible without departing from the sphere and scope of the present disclosure, as defined in the appended claim(s). Accordingly, it is intended that the present disclosure not be limited to the described examples, but that it has the full scope defined by the language of the following claims, and equivalents thereof. The discussion of any example is meant only to be explanatory and is not intended to suggest that the scope of the disclosure, including the claims, is limited to these examples. In other words, while illustrative examples of the disclosure have been described in detail herein, it is to be understood that the inventive concepts may be otherwise variously embodied and employed, and that the appended claims are intended to be construed to include such variations, except as limited by the prior art.

The foregoing discussion has been presented for purposes of illustration and description and is not intended to limit the disclosure to the form or forms disclosed herein. For example, various features of the disclosure are grouped together in one or more examples or configurations for the purpose of streamlining the disclosure. However, it should be understood that various features of the certain examples or configurations of the disclosure may be combined in alternate examples, or configurations. Any example or feature of any section, portion, or any other component shown or particularly described in relation to various examples of similar sections, portions, or components herein may be interchangeably applied to any other similar example or feature shown or described herein. Additionally, components with the same name may be the same or different, and one of ordinary skill in the art would understand each component could be modified in a similar fashion or substituted to perform the same function.

Moreover, the following claims are hereby incorporated into this Detailed Description by this reference, with each claim standing on its own as a separate example of the present disclosure.

As used herein, an element or step recited in the singular and proceeded with the word "a" or "an" should be understood as not excluding plural elements or steps, unless such exclusion is explicitly recited. Furthermore, references to "one example" of the present disclosure are not intended to be interpreted as excluding the existence of additional examples that also incorporate the recited features.

The phrases "at least one," "one or more," and "and/or," as used herein, are open-ended expressions that are both conjunctive and disjunctive in operation. The terms "a" (or "an"), "one or more" and "at least one" can be used interchangeably herein. All directional references (e.g., proximal, distal, upper, lower, upward, downward, left, right, lateral, longitudinal, front, back, top, bottom, above, below, vertical, horizontal, radial, axial, clockwise, and counterclockwise) are only used for identification purposes to aid the reader's understanding of the present disclosure, and do not create limitations, particularly as to the position, orientation, or use of this disclosure. Connection references (e.g., engaged, attached, coupled, connected, and joined) are to be construed broadly and may include intermediate members between a collection of elements and relative to movement between elements unless otherwise indicated. As such, connection references do not necessarily infer that two elements are directly connected and in fixed relation to each other. All rotational references describe relative movement between the various elements. Identification references (e.g., primary, secondary, first, second, third, fourth, etc.) are not intended to connote importance or priority but are used to distinguish one feature from another. The drawings are for purposes of illustration only and the dimensions, positions, order and relative to sizes reflected in the drawings attached hereto may vary.

We claim:

1. An orthopedic broach arranged and configured to prepare an intramedullary canal of a bone, the broach comprising:

a body with a proximal portion and a distal portion, an anterior side, a posterior side opposite the anterior side, a medial side, and a lateral side opposite the medial side, the medial and lateral sides extending between the anterior and posterior sides, the lateral side comprising an anterolateral surface at an intersection of the lateral side with the anterior side and a posterolateral surface at an intersection of the lateral side with the posterior side, wherein:

the medial side comprises a plurality of diamond teeth;

the anterolateral and posterolateral surfaces comprises a plurality of extraction teeth having a different shape as compared to the plurality of diamond teeth;

the anterior side, the posterior side, and at least portions of the lateral side include a plurality of compaction teeth having a different shape as compared to both the plurality of diamond teeth and the plurality of extraction teeth; and the plurality of extraction teeth extend a full length of the body along an anterolateral corner and a posterolateral corner of the body.

2. The broach of claim 1, wherein the plurality of compaction teeth extend substantially a full-length of the lateral side from the proximal portion to the distal portion of the body.

3. The broach of claim 1, wherein each of the plurality of compaction teeth is configured as parallel ledges extending horizontally from the lateral side to the medial side of the anterior and posterior sides of the broach.

4. The broach of claim 1, wherein the plurality of compaction teeth extend substantially a full-length of the anterior and posterior sides from the proximal portion to the distal portion of the body.

5. The broach of claim 1, wherein each of the plurality of extraction teeth are configured as horizontal teeth including an angled cutting flute relief passing therethrough.

6. The broach of claim 1, wherein each of the plurality of diamond teeth include a pointed or spiked tip, the plurality of diamond teeth extending substantially a full-length of the medial side from a proximal end to a distal end of the body.

7. The broach of claim 1, wherein the body includes a connection mechanism arranged and configured to couple the broach to one of a handle and an orthopedic impactor.

8. The broach of claim 1, wherein the body include a distal tip devoid of any teeth.

9. An orthopedic broach arranged and configured to prepare an intramedullary canal of a bone, the broach comprising:

a body with a proximal portion and a distal portion, an anterior side, a posterior side opposite the anterior side, a medial side, and a lateral side opposite the medial side, the medial and lateral sides extending between the anterior and posterior sides, the lateral side comprising an anterolateral surface at an intersection of the lateral side with the anterior side and a posterolateral surface at an intersection of the lateral side with the posterior side, wherein:

the medial side comprises a plurality of diamond teeth including a pointed or spiked tip;

the anterolateral and posterolateral surfaces comprises a plurality of extraction teeth having a different shape as compared to the plurality of diamond teeth; and wherein the plurality of diamond teeth extend substantially a full-length of the medial side from a proximal end to a distal end of the body.

10. The broach of claim 9, wherein the plurality of extraction teeth extend a full length of the body along an anterolateral corner and a posterolateral corner of the body.

11. The broach of claim 10, wherein the anterior side, the posterior side, and at least portions of the lateral side include a plurality of compaction teeth having a different shape as compared to both the plurality of diamond teeth and the plurality of extraction teeth.

12. The broach of claim 9, wherein the body include a distal tip devoid of any teeth.

13. An orthopedic broach arranged and configured to prepare an intramedullary canal of a bone, the broach comprising:

a body with a proximal portion and a distal portion, an anterior side, a posterior side opposite the anterior side, a medial side, and a lateral side opposite the medial side, the medial and lateral sides extending between the anterior and posterior sides, the lateral side comprising an anterolateral surface at an intersection of the lateral side with the anterior side and a posterolateral surface at an intersection of the lateral side with the posterior side, wherein:

the medial side comprises a plurality of diamond teeth including a pointed or spiked tip;

the anterior and posterior sides comprises a plurality of compaction teeth;

the anterolateral and posterolateral surfaces comprises a plurality of extraction teeth; and the lateral side comprises a plurality of compaction teeth;

each of the diamond teeth, the extraction teeth, and the compaction teeth having a different shape as compared to the other teeth; and the plurality of diamond teeth extend substantially a full-length of the medial side from the proximal portion to the distal portion of the body.

14. The broach of claim 13, wherein the plurality of extraction teeth extend substantially a full length of the body along an anterolateral corner and a posterolateral corner of the body.

15. The broach of claim 13, wherein the plurality of compaction teeth extend substantially a full-length of the lateral side from the proximal portion to the distal portion of the body.

16. The broach of claim 13, wherein each of the plurality of compaction teeth is configured as parallel ledges extending horizontally from the lateral side to the medial side of the anterior and posterior sides of the broach.

17. The broach of claim 13, wherein the plurality of compaction teeth extend substantially a full-length of the anterior and posterior sides from the proximal portion to the distal portion of the body.

18. The broach of claim 13, wherein each of the plurality of extraction teeth are configured as horizontal teeth including an angled cutting flute relief passing therethrough.

19. The broach of claim 13, wherein the body include a distal tip devoid of any teeth.

20. An orthopedic broach arranged and configured to prepare an intramedullary canal of a bone, the broach comprising:

a body with a proximal portion and a distal portion, an anterior side, a posterior side opposite the anterior side, a medial side, and a lateral side opposite the medial side, the medial and lateral sides extending between the anterior and posterior sides, the lateral side comprising an anterolateral surface at an intersection of the lateral side with the anterior side and a posterolateral surface at an intersection of the lateral side with the posterior side, wherein:

the medial side comprises a plurality of diamond teeth;

the anterolateral and posterolateral surfaces comprises a plurality of extraction teeth having a different shape as compared to the plurality of diamond teeth; and the plurality of extraction teeth extend a full length of the body along an anterolateral corner and a posterolateral corner of the body.

21. The broach of claim 20, wherein the anterior side, the posterior side, and at least portions of the lateral side include a plurality of compaction teeth having a different shape as compared to both the plurality of diamond teeth and the plurality of extraction teeth.

22. The broach of claim 20, wherein the plurality of extraction teeth extend a full length of the body along an anterolateral corner and a posterolateral corner of the body.

23. The broach of claim 20, wherein the body include a distal tip devoid of any teeth.

\* \* \* \* \*